(12) United States Patent
Boss

(10) Patent No.: US 10,364,453 B1
(45) Date of Patent: Jul. 30, 2019

(54) DETECTING OF BACTERIA USING FLUORESCENTLY-LABELED PHAGE IMMOBILIZED ON AN OPTICALLY TRANSPARENT SURFACE

(71) Applicant: Pamela A Boss, San Diego, CA (US)

(72) Inventor: Pamela A Boss, San Diego, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 294 days.

(21) Appl. No.: 13/758,476

(22) Filed: Feb. 4, 2013

(51) Int. Cl.
*C12Q 1/10* (2006.01)
*C12Q 1/70* (2006.01)

(52) U.S. Cl.
CPC .................... *C12Q 1/10* (2013.01); *C12Q 1/70* (2013.01)

(58) Field of Classification Search
None
See application file for complete search history.

(56) References Cited

U.S. PATENT DOCUMENTS

| | | | |
|---|---|---|---|
| 4,868,130 A * | 9/1989 | Hargreaves | B01L 3/502 435/7.7 |
| 7,632,637 B1 | 12/2009 | Boss | |
| 2002/0127547 A1 * | 9/2002 | Miller | 435/5 |
| 2004/0137430 A1 * | 7/2004 | Anderson et al. | 435/5 |
| 2004/0191859 A1 * | 9/2004 | Tabacco et al. | 435/69.1 |
| 2005/0255043 A1 * | 11/2005 | Hnatowich et al. | 424/9.1 |
| 2009/0117536 A1 * | 5/2009 | Mattey | C12Q 1/04 435/5 |

OTHER PUBLICATIONS

Pamela A. Mosier-Boss et al., Use of Fluorescently Labeled Phage in the Detection and Identification of Bacterial Species, Applied Spectroscopy, vol. 57, No. 9, 2003, pp. 1138-1144.

* cited by examiner

*Primary Examiner* — Bao Thuy L Nguyen
*Assistant Examiner* — Ellen J Marcsisin
(74) *Attorney, Agent, or Firm* — NavInfWarCen Pacific; Arthur K. Samora; Kyle Eppele

(57) ABSTRACT

A device and method for detecting bacteria in a sample can include an optically transparent substrate and a phage that is known to react with the bacteria being detected. The phage can be tagged with a fluorescent tag such as DAPI or SBYR® Gold cyanine dye. Once fluorescently tagged, the phage-substrate combination can be illuminated with a light source, at a wavelength that corresponds to an excitation wavelength for the fluorescent tag to establish a baseline intensity for the device. The device can then be exposed to the sample and illuminated to establish a test intensity. The bacteria to be detected can be deemed as being present if the test intensity is less than the baseline intensity.

5 Claims, 9 Drawing Sheets

Before: Dip stick fully Covered with fluorescently labeled phage

Phage bind to host bacterium

Phage with DAPI stained DNA

After: Bacteria has lyzed. See a decrease in fluorescently labeled phage on dip stick Phage that had injected its DAPI stained DNA into host bacterium See a decrease in intensity as fewer fluorescently labeled phage remain on dip stick. Signal decreases in proportional to number of bacteria.

DETECTING OF BACTERIA USING FLUORESCENTLY-LABELED PHAGE IMMOBILIZED ON AN OPTICALLY TRANSPARENT SURFACE

FEDERALLY-SPONSORED RESEARCH AND DEVELOPMENT

This invention (Navy Case No. 101321) is assigned to the United States Government and is available for licensing for commercial purposes. Licensing and technical inquires may be directed to the Office of Research and Technical Applications, Space and Naval Warfare Systems Center, Pacific, Code 72120, San Diego, Calif. 92152; voice (619) 553-5118; email ssc rac T2navv.mil.

FIELD OF THE INVENTION

The present invention pertains generally to detection of bacteria. More specifically, the present invention pertains to the optical detection of bacteria using a fluorescently-labeled phage, which has been immobilized on an optically transparent surface.

BACKGROUND OF THE INVENTION

Phages are viruses whose hosts are bacterial cells. The phages identify their hosts through host cell-specific receptor molecules, which are located on the outside of the host cell. Once the phages find their specific receptors, they bind to the bacterial cell and inject their nucleic acid into the cell. The phage nucleic acid then takes over the host cell's machinery to make large amounts of phage components. The phage components are then assembled into new phages. The phages then direct production of an enzyme that breaks down the bacteria cell wall, which causes the bacteria to lyse, which further frees new phages. Phage lysis assays are known in the prior art for the detection and identification of various bacterial pathogens.

Antibodies have also been used to discriminate bacterial species. However there are a number of advantages to using phage-based detection schemes, as opposed to using antibody-based schemes. More specifically, antibodies are bare protein molecules. As such, they are potential food sources for bacteria. Bacterial "grazing" of antibody-coated magnetic microparticles has been observed. Such grazing can result in false positives, when compared to a phage-based scheme. Other limitations of antibody-based immunoassays include antibody manufacturability and instability.

Each bacterial species has at least one phage that will prey upon it. Phages can be readily obtained from phage libraries. One such library is the Felix D'Herelle Reference Center for Bacterial Viruses at Laval University in Quebec, Canada. This library has a collection of approximately 500 different species of phage. Phages are very robust and are not as sensitive to environmental conditions (pH, temperature, salinity, etc.) as antibodies are. Large quantities of phages can be easily cultured and purified. Additionally, the purified phage exhibits a long shelf life relative to antibodies.

In view of the above, it is an object of the present invention to provide a device and method for detecting bacteria using fluorescently-labeled phage immobilized on an optically transparent surface that minimizes false positives. Another object of the present invention is to provide a device and method for detecting bacteria using fluorescently-labeled phage immobilized on an optically transparent surface that is stable and that can easily be stored for extended periods of time prior to use. Still another object of the present invention is to provide a device and method for detecting bacteria using fluorescently-labeled phage immobilized on an optically transparent surface that can use multiple phages at the same time, to provide for testing of multiple species of bacteria at the same time, and that can distinguish between different types of bacteria. Yet another object of the present invention to provide a device and method for detecting bacteria using fluorescently-labeled phage immobilized on an optically transparent surface that is easy to manufacture in a cost-effective manner, and that is easy to use by remote operators in the field.

SUMMARY OF THE INVENTION

A device and method for detecting bacteria in a sample according to some embodiments can include an optically transparent substrate and a phage that can be chosen according to the bacteria being detected. A phage that is known to react with the bacteria to be detected can be selected, and the phage can be immobilized head down on the substrate. In some embodiments, the phage can be P22 if the bacteria that is proposed for detection is salmonella.

The phage is further tagged with a fluorescent tag. Suitable fluorescent tags can include 4',6-diamidino-2-phenylindole (DAPI) or SBYR® Gold cyanine dye. Once fluorescently tagged, the phage-substrate combination can be illuminated at a wavelength corresponding to an excitation wavelength for the fluorescent tag to establish a baseline intensity for the device. The device can then be exposed to the sample and illuminated to establish a test intensity. The bacteria to be detected can be deemed as being present if the test intensity is less than the baseline intensity.

BRIEF DESCRIPTION OF THE DRAWINGS

The novel features of the present invention will be best understood from the accompanying drawings, taken in conjunction with the accompanying description, in which similarly-referenced characters refer to similarly-referenced parts, and in which.

DETAILED DESCRIPTION OF THE EMBODIMENTS

Figure 1:
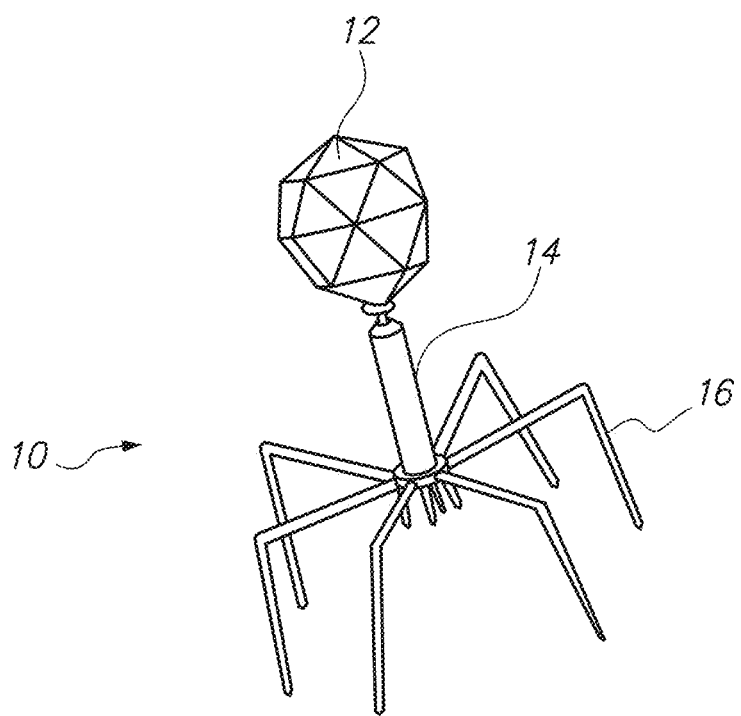
FIG. 1 is a depiction of a phage as commonly understood in the prior art.
Figure 2:
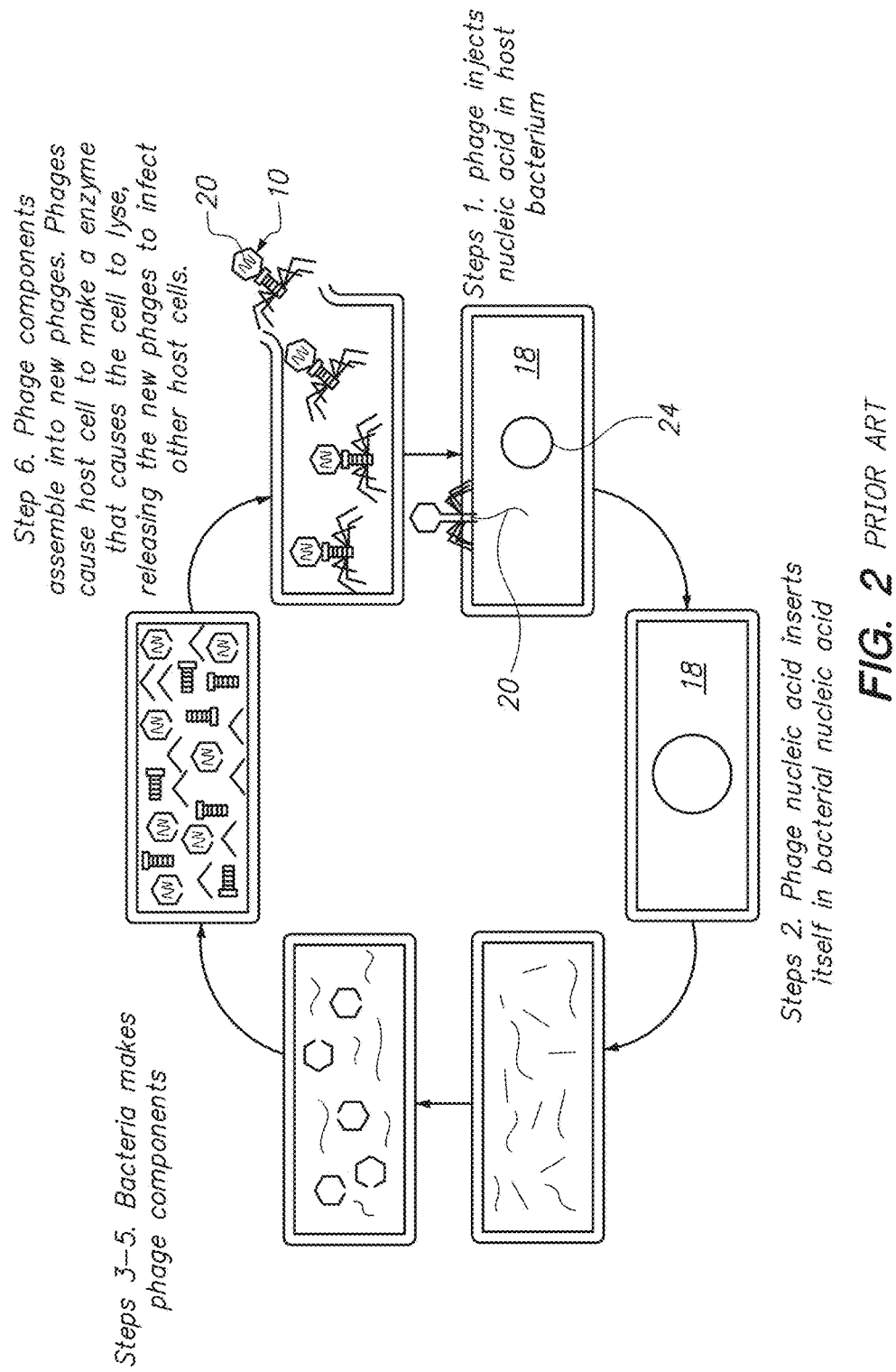
FIG. 2 is a drawing that illustrates the lysis cycle of phage in bacteria, as commonly understood in the prior art.

In brief overview, and referring initially to FIGS. 1 and 2, a phage 10 as known in the prior art is shown. Phages 10 can consist of a long nucleic acid molecule (either DNA or RNA) 20 (see FIG. 2) that is coiled within a polyhedral-shaped protein head 12. Phages have a tail 14 that is attached to the head 12. Tail fibers 16 that extend from the tail 14 attach the phage to the bacterium 18 (depicted in FIG. 2). As shown in FIG. 2, the phage 10 can inject phage nucleic acid 20 into the host bacterium nucleic acid (represented by reference character 24) of bacterium 18. The phage nucleic acid 20 can insert itself into the bacterial nucleic acid 24 (as known in the prior art), which can further cause the host cell to make new phages and an enzyme that causes the cell to lyse which can release new phages to infect other host cells, as depicted in FIG. 2. This manner in which this lyse process can be taken advantage of is described more fully below.

Phages can be readily obtained from phage libraries. One such library is the Felix D'Herelle Reference Center for Bacterial Viruses at Laval University in Quebec, Canada. This library has a collection of approximately 500 different species of phages. Other phage libraries could also be accessed to practice the devices and methods of the invention according to several embodiments. Phages are very robust and are not as sensitive to environmental conditions (pH, temperature, salinity, etc.) as antibodies are. Large quantities of phage can be easily cultured and purified. Additionally, the purified phages can exhibit a long shelf life.

Figure 3:
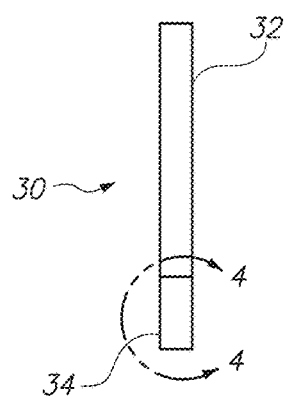
FIG. 3 is side-elevational view of the device of the present invention, according to several embodiments.
Figure 4:
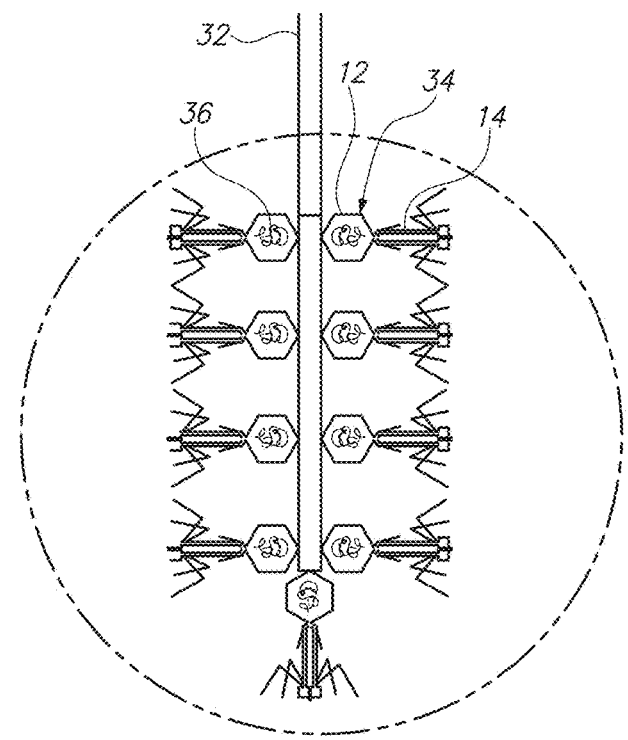
FIG. 4 is a greatly enlarged view of the lower portion of the device, taken along line 4-4 in FIG. 3, which can illustrate the structural relationship between the phages and the substrate.

Referring now to FIGS. 3 and 4, the measurement device according to several embodiments is shown and is designated by reference character 30. As shown the measurement device 30 can include an optically transparent substrate 32 and a phage 34 that can be attached to a portion of the optically transparent substrate 32.

For reasons that will become apparent, it is important to mobilize the phage 34 so that is it "head down" on the optical substrate. For purposes of this disclosure, "head down" means that the head 12 of phage 34 is in contact with substrate 32, with tail 14 facing outward from substrate 32. One way to do this is described in U.S. Pat. No. 7,632,637, which issued to Boss et al. for an invention entitled "Technique for Orienting and Binding Phage for Bacteria Detection", and which is assigned to the same assignee as the present invention. The contents of the '637 patent are hereby incorporated by reference herein.

FIG. 4 also illustrates phage DNA/RNA that has been tagged with a fluorescent nucleic acid stain (hereinafter, "fluorescent tag" and "fluorescent nucleic acid stain" are used interchangeably and can be taken to mean that same thing). The fluorescent tag in FIG. 4 is illustrated by reference character 36. An example of a fluorescent nucleic acid stain to use is DAPI. Another fluorescent tag 36 that could be used is SYBR® Gold (SYBR® is a registered trademark of Molecular Probes, Inc.). Other fluorescent tags could also be used.

Figure 5A:
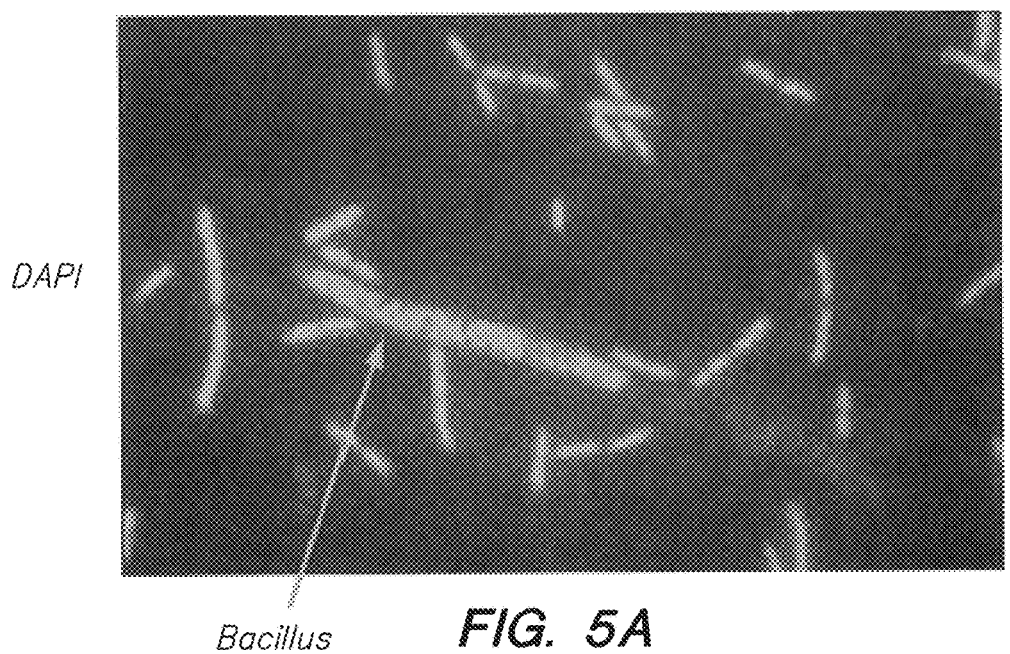
FIGS. 5A-5B are color photographs of bacteria and phages that have been tagged with DAPI fluorescent tag and SYBR® gold fluorescently labeled phage DNA and magnified 1000×.
Figure 5B:
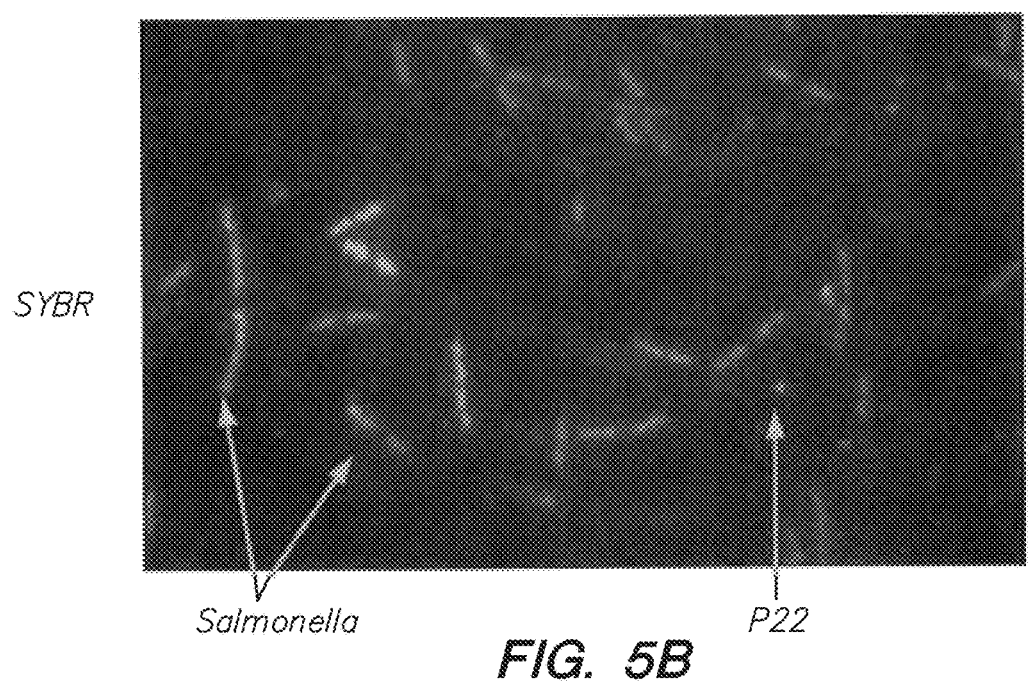

As described above and shown in FIG. 2, it has been shown in the prior art that phages 10 are able to inject their fluorescently labeled DNA/RNA into its host cell. FIGS. 5A and 5B are color photographs of this phenomenon. FIGS. 5A and 5B illustrate samples of two bacterial species, *Salmonella* and *Bacillus megaterium*, and a phage whose host is *Salmonella*, P22, was prepared. The DNA of P22 was fluorescently labeled with the nucleic acid SYBR® gold. Another nucleic acid, DAPI, was also added to the sample. After incubation for 10 minutes, the sample was filtered onto a ceramic filter. Images were taken in both the DAPI and SYBR channels. The DAPI stains the DNA of the two bacterial species and the phage. Consequently the DAPI channel shows all three species. In the SYBR channel, the source of the SYBR is through the fluorescently labeled DNA of phage P22. In this channel, only P22 and *Salmonella* are observed. The phage P22 has injected its fluorescently labeled DNA inside its host, *Salmonella*.

Figure 6:
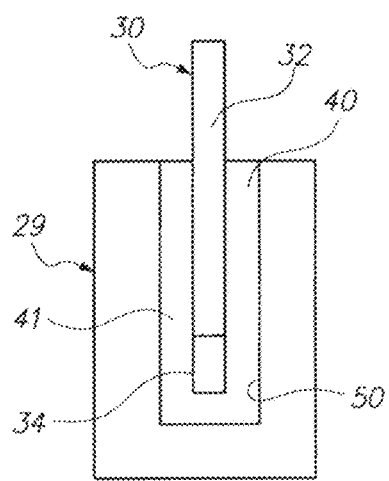
FIG. 6 is the cross-sectional view of the device of FIG. 3 when placed in a container including a sample, with portions of the container removed for clarity.
Figure 7:
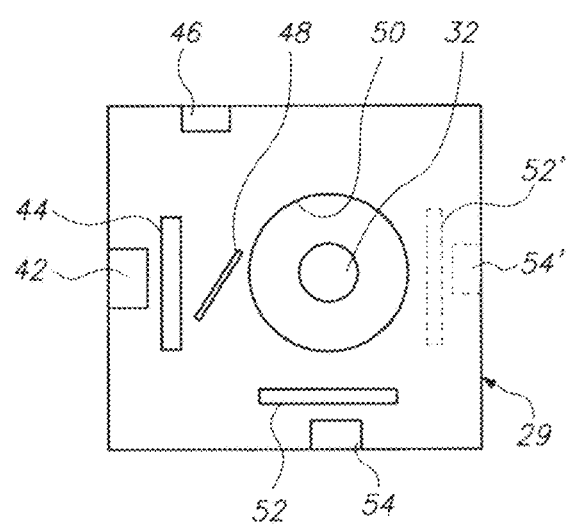
FIG. 7 is a top plan view of the device of FIG. 6.

Referring now to FIGS. 6 and 7, a sensor 29 according to several embodiments is shown. As shown sensor 29 can include a container 38 that is formed with a cavity 40 having a partially mirrored surface 50. A light source 42 that emits at a known excitation wavelength can be activated the fluorescent tag 36 to fluoresce. A collimating lens and excitation filter 44 can be included to filter the light source 42 to ensure that the fluorescent tags 36 are illuminated at the proper wavelength. For example, in several embodiments the fluorescent tag can be DAPI, and light source can be used to excite the fluorescence of the DAPI. The light source 42 can be a light emitting diode (LED) that emits at the excitation wavelength for DAPI or a xenon arc lamp. A lens can collimate the light. An excitation filter allows light, of the appropriate wavelength to excite DAPI (roughly in the 350-375 nanometer wavelength range), into the chamber. A beamsplitter 48 can send part of the light to a photodiode 46 that monitors the light intensity for feedback purposes, i.e., to verify for the user (not shown) that the sensor 29 provide a baseline intensity of illumination that is constant.

The light enters the sample chamber of sensor 29 and hits the measurement device 30, which causes the DAPI on the phage nucleic acid to fluoresce. The mirrored surface 50 of the sample chamber 40 can increase the efficiency at which the light is collected. A collecting lens 54 collects the light emitted from the chamber. An emission filter 54 blocks the excitation light and only lets the light due to the tag fluorescence hit the detector 54. For DAPI fluorescent tags, the emission filter would pass light in the range of 425-500 nanometer wavelength range. But the excitation and emission filter structures are chosen to the fluorescent tag that is chosen for the device and methods of the invention according to several embodiments. Also, for embodiments that do not have a mirror, emission filter 52' and detector 54' can be placed opposite transparent substrate 32 in a line-of-sight relationship with light source 42, as shown in phantom in FIG. 7.

Figure 8:
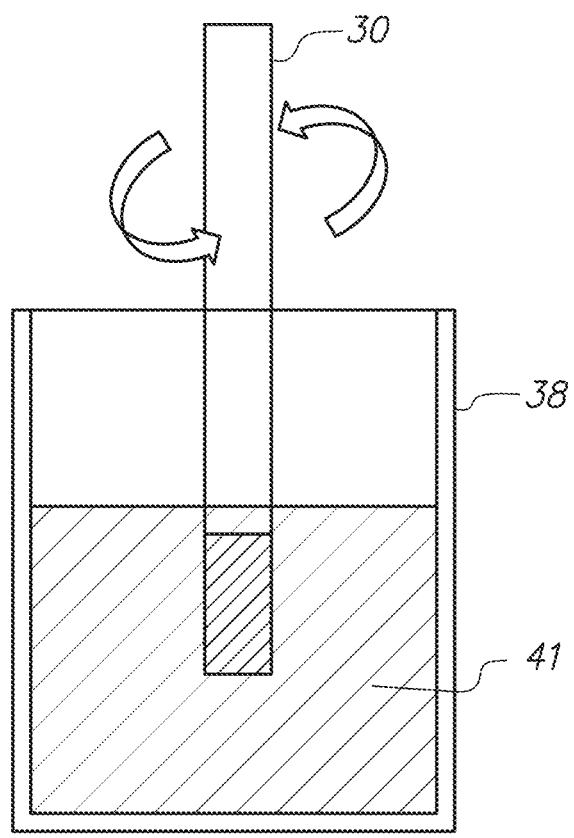
FIG. 8 depicts how sampling is done according to several embodiments of the invention.

Measurement device 30 can be placed in chamber 40 and light 42 can be activated to establish a baseline intensity for the device. Measurement device 30 is then taken out of sensor 29 and is then inserted in a container 38 containing the sample 41, FIG. 8. The sample 41 can be either water, food, or a slurry of food in water. The measurement device 30 can be swirled around in the sample 41. Sampling time can vary. After sampling, the measurement device 30 can be rinsed and can be placed in an incubation tube (not shown in the Figures) to allow the phage to inject their fluorescent tagged DNA into the host bacteria and causing the host bacteria to lyse.

Figure 9A:
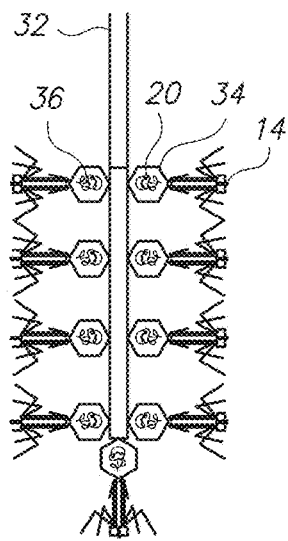
FIGS. 9A-9C depict the phage activity in binding to the host bacterium during operation of the device according to several embodiments.
Figure 9B:
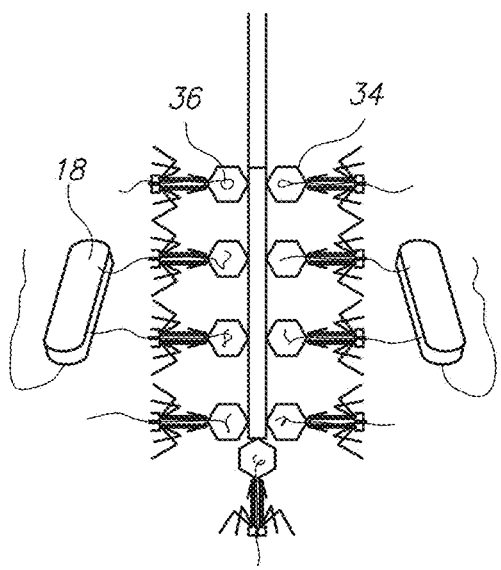
Figure 9C:
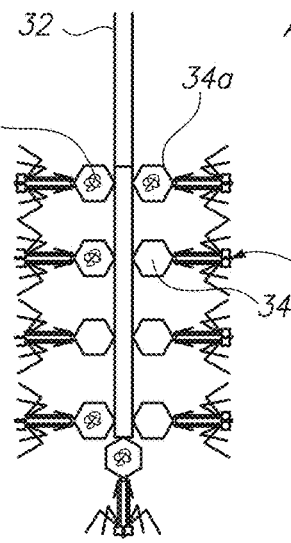

FIGS. 9A-9C and 10A-10B illustrate what can happen to phages 34 on the substrate 32 (the dip stick) before and after interaction of phage 34 with the host bacteria 18. FIG. 9A is representative of phages 34 that have been immobilized head down on substrate 32 as describe above, prior to any exposure to sample 41. The phage nucleic acid 20 has been tagged with fluorescent tags 36, but there has not been any interaction with bacteria from a sample 41, so all of the phages 34 contain fluorescently tagged DNA 24. Next, device can be exposed to a sample 41 as described above. At this point, the phage 34 has bound to its host bacterium 18 as shown in FIG. 9B. Once this occurs (and while the exposed phage-substrate combination is incubating in an incubation tube in several embodiments), the phage 34 injects its fluorescently labeled DNA 24 inside any host bacteria 18 it has captured during the sampling. The phage DNA takes over the machinery of the host bacterium and begins replicating itself. Eventually the bacterium cell will lyse. As shown in FIG. 9C, this will result in a 32 where some phage 34, that did not bind to the host bacterium, still retain their DAPI-stained nucleic acid 24 and phage 34, as depicted by phage 34a. But the phages 34 that did bind to the host bacterium and caused the bacterium cell to lyse, are now empty shells, as depicted by phage 34b.

Figure 10A:
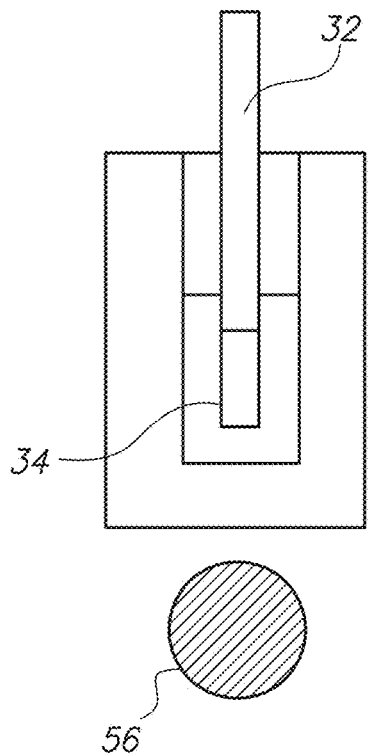
FIGS. 10A and 10B are color photographs that illustrates the baseline intensity and test intensity, respectively, for the device having a sample that has tested positive for the bacteria that is intended to be detected; and, FIG. 11 is a block diagram which can be used to describe the methods of the present invention according to several embodiments.
Figure 10B:
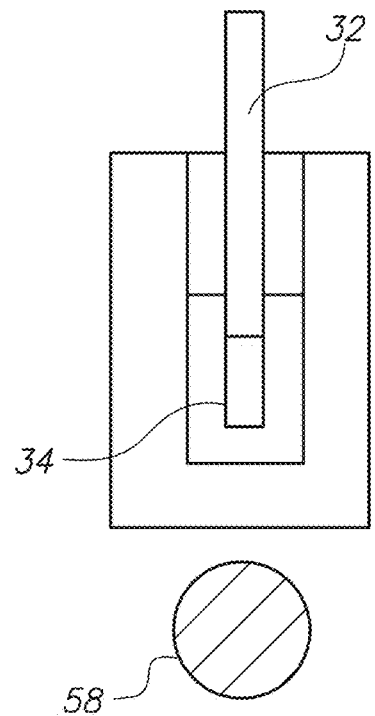

Because there are not as many fluorescently-tagged phages 34 on the measurement device 30 (due to injection of DAPI-stained, phage nucleic acid from the immobilized phages 34 into the bacteria 18 during lysis), the resultant overall fluorescence from the substrate 32 decreases, FIGS. 10A and 10B illustrate this phenomenon. FIG. 10A illustrates a baseline intensity 56, while FIG. 10B illustrates a test intensity 58 for a sample 41 that has tested positive for the bacteria 18 under test. Since there has been a loss in DAPI-stained, phage nucleic acid. The decrease in fluorescence can be proportional to the number of bacterial cells captured by the phage on the measurement device 30. Stated differently, once the baseline intensity 56 is known, the test intensity 58 can be measured in a manner known in the art to determine not only the presence of the bacteria that is being detected, but the amount on bacteria that is present, based the decrease of the test intensity 58 relative to the baseline intensity 56. The lysate in the incubation tube (not shown in the Figures), can be saved for further confirmatory analysis.

Figure 11:
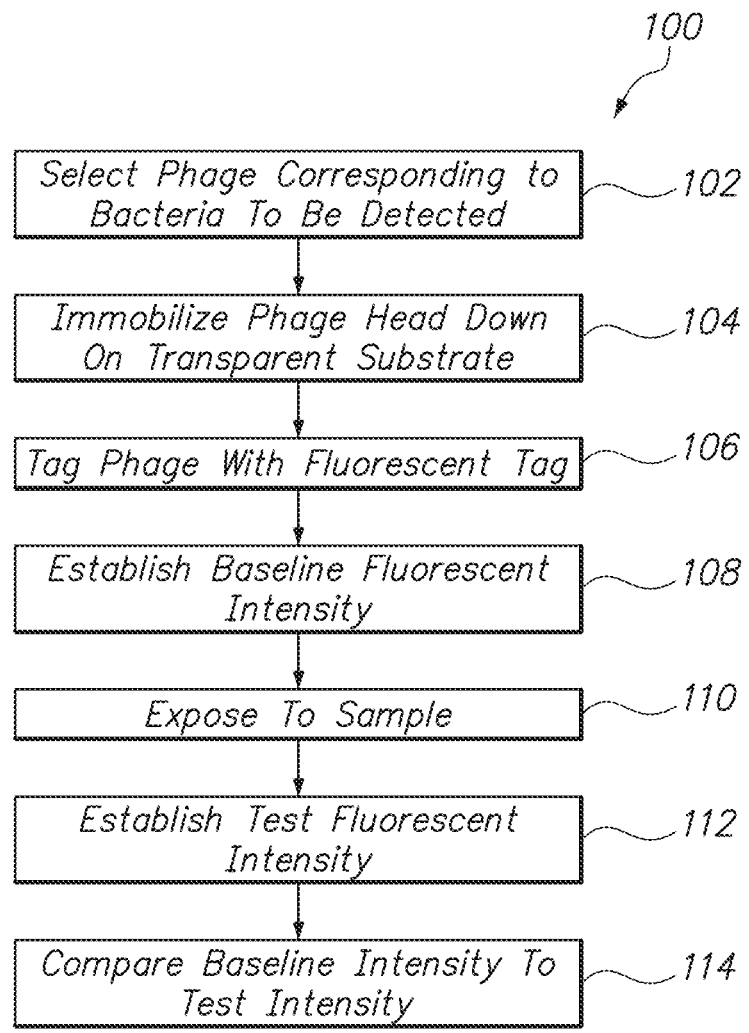

Referring now to FIG. 11, a diagram which depicts steps that can be taken to accomplish the methods according to several embodiments is shown and is generally designated by reference character 100. As shown, the method 100 can include the initial step of selecting the appropriate phage for the bacteria that is to be detected, as indicated by step 102. The phage to be selected should be phages that will react with the receptors for the bacteria to be detected, as described above. Once selected, the phage can be obtained from an exemplary library, as described above. Referring back to FIG. 11, the methods according to several embodiments can further include the step of immobilizing the phage 34 head down on a transparent substrate 32, as shown by block 104, and tagging the phage 34 with a fluorescent tag (block 106). Steps 104 and 106 can be accomplished in any order, but it should be appreciated that for embodiments where multiple bacteria are to be detected using multiple phages, the tagging of the phages (step 106) must be accomplished prior to immobilizing the phages head down on substrate 32 (step 104).

Once the phages are immobilized, the methods can further include the step of illuminating the phage with a light source to establish a baseline intensity for the methods, as indicated by step 108. The illumination steps can be accomplished at an excitation wavelength(s) for said fluorescent tag that was (were) used in step 106. Once the baseline intensity is established, the phage is then exposed to the sample 41, as indicated by step 110 in FIG. 11. The device is then illuminated to establish a test intensity for the device, as depicted by block 112 in FIG. 11. The test intensity is then compared to the baseline intensity, as shown by step 114. If the test intensity is less than the baseline intensity, then the sample is deemed to have contained the bacteria that being tested for. The differences in intensity can be used to determine how much bacteria is present using instruments as known in the prior art.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for detecting bacteria in a sample, said method comprising the steps of:
    A) selecting a phage that is known to react with said bacteria to be detected said phage having nucleic acid;
    B) immobilizing said phage head down on a transparent substrate;
    C) tagging said phage nucleic acid with a fluorescent nucleic acid tag;
    D) illuminating said phage from said step C) with a light source;
    E) establishing a baseline fluorescence intensity for said illuminated phage from said step D);
    F) exposing said tagged phage from said step C) to said sample to allow said tagged phage to lyse said bacteria;
    F1) removing said substrate from said step F) from said sample;
    G) illuminating said substrate from said removing step to establish a test fluorescence intensity;

H) comparing said test fluorescence intensity to said baseline fluorescence intensity, and, I) deeming said bacteria to be present in said sample when said test fluorescence intensity is less than said baseline fluorescence intensity.

2. The method of claim 1 wherein said bacteria is *Salmonella* and said phage in said step A) is P22.

3. The method of claim 1 wherein said step C) is accomplished with 4',6-diamidino-2-phenylindole (DAPI) dye fluorescent tag.

4. The method of claim 3 wherein said step D) is accomplished using a light source that emits light at a wavelength corresponding to an excitation wavelength for said fluorescent tag.

5. The method of claim 4, wherein said step E) is accomplished using a first optical detector for measuring said baseline intensity.

* * * * *